(12) United States Patent
Gondhalekar et al.

(10) Patent No.: US 6,837,184 B2
(45) Date of Patent: Jan. 4, 2005

(54) PROGRAMMABLE ELECTRONIC MAZE FOR USE IN THE ASSESSMENT OF ANIMAL BEHAVIOR

(75) Inventors: Vijay Gondhalekar, Hawthorne, NY (US); Daniela Brunner, Riverdale, NY (US)

(73) Assignee: Psychogenics, Inc., Hawthorne, NY (US)

( * ) Notice: Subject to any disclaimer, the term of this patent is extended or adjusted under 35 U.S.C. 154(b) by 12 days.

(21) Appl. No.: 10/212,834

(22) Filed: Aug. 5, 2002

(65) Prior Publication Data

US 2003/0024482 A1 Feb. 6, 2003

Related U.S. Application Data

(60) Provisional application No. 60/310,430, filed on Aug. 6, 2001.

(51) Int. Cl.[7] ............................. A01K 1/03; E04B 1/346
(52) U.S. Cl. ........................................... 119/421; 52/65
(58) Field of Search .............................. 119/416, 417, 119/421, 452; 273/110, 109; 472/62, 86; 463/15; 52/65

(56) References Cited

U.S. PATENT DOCUMENTS

| | | | |
|---|---|---|---|
| 3,100,473 A | | 8/1963 | Kissel |
| 3,516,389 A | * | 6/1970 | Meyer ........................ 119/417 |
| 3,706,455 A | * | 12/1972 | Meyer ........................ 273/110 |
| 3,803,571 A | | 4/1974 | Luz |
| 3,857,364 A | * | 12/1974 | Miller, Jr. ................... 119/417 |
| 3,974,798 A | | 8/1976 | Meetze, Jr. |
| 4,182,514 A | | 1/1980 | Magid et al. |
| 4,240,638 A | | 12/1980 | Morrison et al. |
| 4,311,310 A | | 1/1982 | Dankman et al. |
| 4,323,242 A | | 4/1982 | Rosenfeld |
| 4,326,719 A | | 4/1982 | Tran et al. |
| 4,337,726 A | | 7/1982 | Czekajewski et al. |
| 4,511,143 A | | 4/1985 | Sankrithi |
| 4,574,734 A | | 3/1986 | Mandalaywala et al. |
| 4,850,592 A | * | 7/1989 | Winter ....................... 273/109 |
| 5,095,852 A | | 3/1992 | Hoover |
| 5,393,074 A | * | 2/1995 | Bear et al. .................... 472/62 |
| 5,549,884 A | | 8/1996 | Weinberger et al. |
| 5,816,256 A | | 10/1998 | Kissinger et al. |
| 5,915,332 A | * | 6/1999 | Young et al. ................ 119/421 |
| 5,969,755 A | | 10/1999 | Courtney |
| 6,095,927 A | * | 8/2000 | Malone ........................ 472/62 |
| 6,123,047 A | * | 9/2000 | Sakai .......................... 119/417 |
| 6,273,026 B1 | * | 8/2001 | Ferster et al. ................ 119/421 |
| 6,675,538 B2 | * | 1/2004 | Candio ......................... 52/65 |
| 2002/0170241 A1 | * | 11/2002 | Candio ......................... 52/65 |

* cited by examiner

Primary Examiner—Teri P. Luu
Assistant Examiner—Elizabeth Shaw
(74) Attorney, Agent, or Firm—Morgan & Finnegan, LLP; Kenneth H. Sonnenfeld

(57) ABSTRACT

A system and method for studying a test subject includes monitoring the test subject as it traverses through a programmable maze. The test subject may be under the influence of experimental drugs or genetic manipulation. The dynamic maze can be changed automatically or manually to test the abilities of the test subject. The dynamic maze comprises of a starting point, an ending point, and an electronically programmable floor capable of constructing various obstacles and passageways. The programmable floor may be programmed by a human user using an interface, or it may be programmed by an automated control system that programs the maze in accordance with the ability of the test subject to traverse the maze. Various devices are incorporated with the use of the maze to monitor the activities and welfare of the test subject.

79 Claims, 12 Drawing Sheets

PROGRAMMABLE ELECTRONIC MAZE FOR USE IN THE ASSESSMENT OF ANIMAL BEHAVIOR

This application claims the benefit of Provisional Application No. 60/310,430, filed Aug. 6, 2001.

FIELD OF THE INVENTION

The present invention relates to systems and methods performing tests on laboratory animals.

BACKGROUND OF THE INVENTION

A critical stage in the development of a new drug or genetic treatment is the animal trial stage. In this stage, the drug is administered to one or more animal test subjects, often laboratory mice, in order to determine possible drug benefits and side effects. Information concerning an animal's behavior in response to a drug, including cognitive function, can provide valuable information concerning the efficacy or safety of the drug.

One device used in the art to obtain behavioral information of an animal test subject during a drug trial is a maze. An animal test subject is placed in a physical construction of obstacles and passageways. By evaluating the animal's ability to correctly navigate the maze, such as the time it takes for the animal to traverse the maze, investigators can gain insight into the effect of a drug on the behavior of the animal.

In a controlled maze test, it may be advantageous to test subjects with a number of different mazes. For example a test animal, due to the effects of a drug administered to it, may be unable to traverse a first maze. Under such circumstances, investigators may wish to test the animal with a different, perhaps less complex, maze. Currently, the only way to accomplish this is to physically replace one maze with another. Such physical replacement can be tedious and cumbersome to the investigator. Perhaps more importantly, it can affect the outcome of the test. For example, the time it takes for the investigators to physically replace one maze with another may allow the drug to wear off or otherwise decrease in intensity in the body of the animal test subject. In addition, transferring the animal from one maze to another may change the response of the animal as a result of its interaction with the investigator.

SUMMARY OF THE INVENTION

A dynamic maze is illustrated having at least one removable obstacle. The obstacle is under the control of a programmable system that configures the maze by inserting or removing the obstacle into the maze. The re-configuration of the design of the maze is accomplished without intervention from the user. The re-configuration can be based on the test subject's ability to traverse through the maze as well as other variable such as the test subject's behavior. Various removable obstacles can be utilized in the dynamic maze. The obstacles are controlled by a controller that may or may not have a user interface. The controller contains logic that allows the maze to re-configure the positions of the obstacles within the maze. The maze rapidly re-configures for the measurement of different behavioral responses and/or conditioning of a test subject. The invention also allows for the generation, acquisition, and maintenance of database systems containing information supplied by the dynamic maze. Thus, associations, patterns, and trends may be classified and predicative models may be obtained of the behavior of the test subject. The invention also allows the continuous collection of behavioral data concerning the test subject thereby providing a more efficient, user-independent, and cost-effective approach than traditional behavioral tests.

These aspects and other objects, features, and advantages are described in the following Detailed Description which is to be read in conjunction with the accompanying drawings.

DETAILED DESCRIPTION OF THE INVENTION

This invention provides a device for testing and monitoring behavioral, including cognitive and physical attributes, of test subjects. The invention also provides a means for conditioning the test subject. The device of this invention is particularly useful for evaluating the influence of an experimental drug or genetic treatment on a test subject so that the effect of the drug or treatment can be qualitatively and quantitatively measured. The device comprises a dynamic maze capable of various configurations so that the obstacles and the passageways in the maze may be dynamically reconfigured. In one embodiment, this dynamic maze constitutes active flooring of an enclosure for the animal test subject. Depending on the implementation, the enclosure may be any structure which is effective for maintaining the test subject in a definable space. Examples include a cage made up with metal bars and an enclosure produced from transparent plastic panels that permit visual observation of the animal test subjects contained within. It is understood that the cage can be any housing, habitat or confined area that houses the test subject. It is further understood that the systems and methods described herein can include unconfined or open areas such as dens, parklands, sanctuaries and the like.

The maze typically comprises of a starting point, a programmable floor, and an end point. In a preferred embodiment, the starting point may be a nesting area for example. The end point may be a food and water area or some other reward for the test subject that provides the test subject with an incentive to traverse the maze. In alternate embodiments the starting point may present an unpleasant object or stimulus, such as an unpleasant odor, to a test subject. In such a case the subject's incentive to traverse the maze might be to escape the unpleasant object or stimulus. In such cases the end point need not include a reward.

Mazes of the present invention are defined by obstacles and passageways. Passageways allow for the passage of a test subject, while obstacles prevent or impede passage.

Obstacles that prevent passage may be walls that are too tall for a test subject to climb or obstacles that a test subject is physically capable of surmounting but has been trained not to. For example, a test subject may be trained not to enter areas bathed in light. Either by physically preventing passage or indicating that passage is not allowed, such obstacles act as absolute barriers to a test subject's movement.

Obstacles that impede passage, such as certain configurations of blocks or stilts, allow for the passage of a test subject only if it displays a certain level of skill or dexterity. For example, crossing stilts might require a test subject to move each foot from one stilt to the next without letting it fall into the space between two stilts.

Figure 2A:
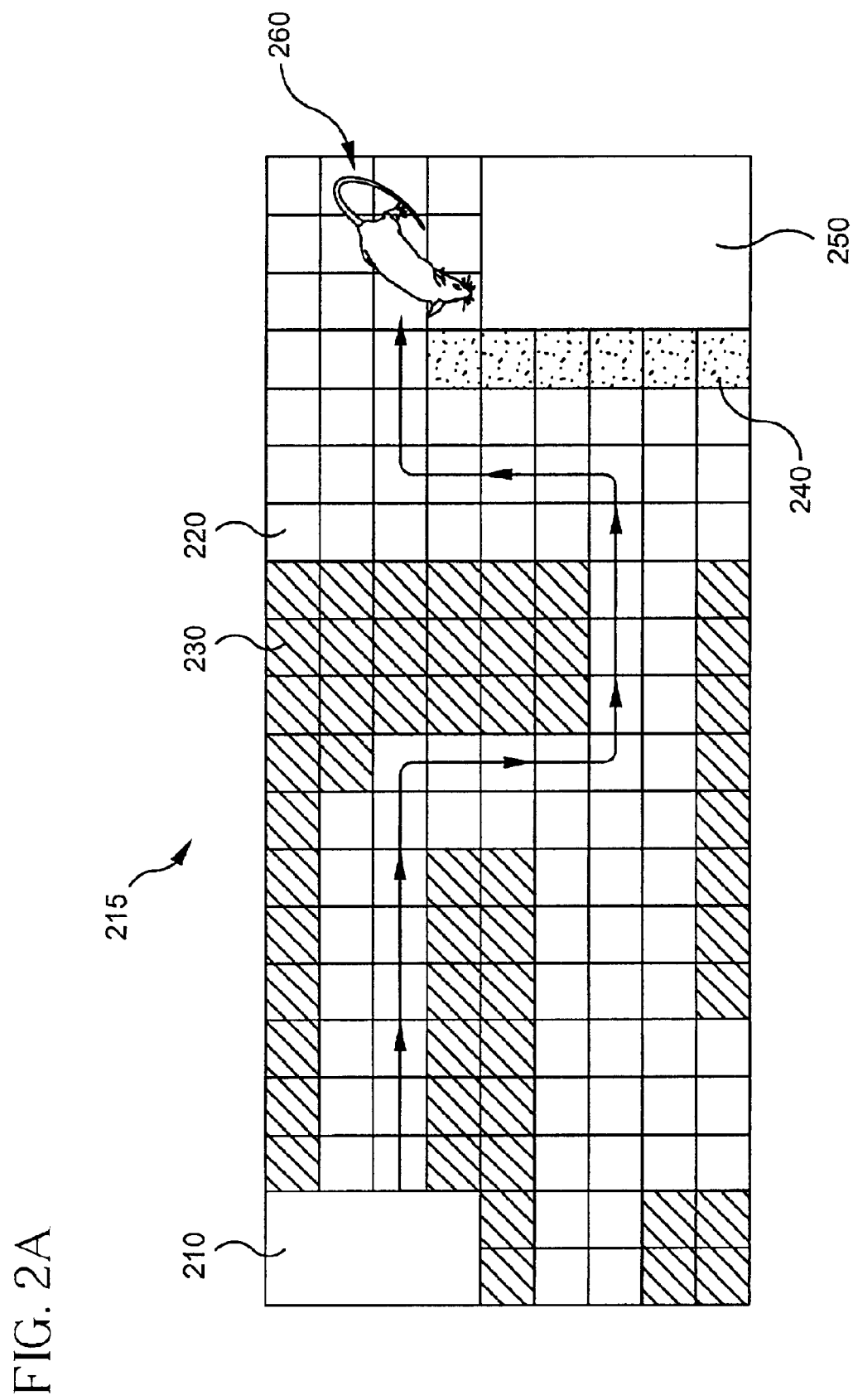
FIG. 2A is a top view of the maze shown in FIG. 1.

Several forms of dynamically-alterable obstacle/passageway elements are provided by the present invention. One such element, shown in FIG. 2A, is a floor plate. When inactivated, the plate acts as a passageway. When activated, the plate acts as an obstacle which prevents or impedes passage. The plate may be activated, for example, by turning on an integrated light source or shock-providing mechanism. The shock-providing mechanism might, for example, be adjustable so that a high level of shock prevents passage while a lower level of shock impedes passage.

Another such element, shown in FIG. 3, is a wall which rises from the floor of the maze, wherein the wall rises to a predetermined height. Setting the height such that the test subject is incapable of climbing the wall creates an obstacle that prevents passage. Setting the height such that the test subject is capable of climbing the wall with effort creates an obstacle that impedes passage. A passageway or portion thereof may be created by setting the wall to not rise from the floor.

Figure 4:
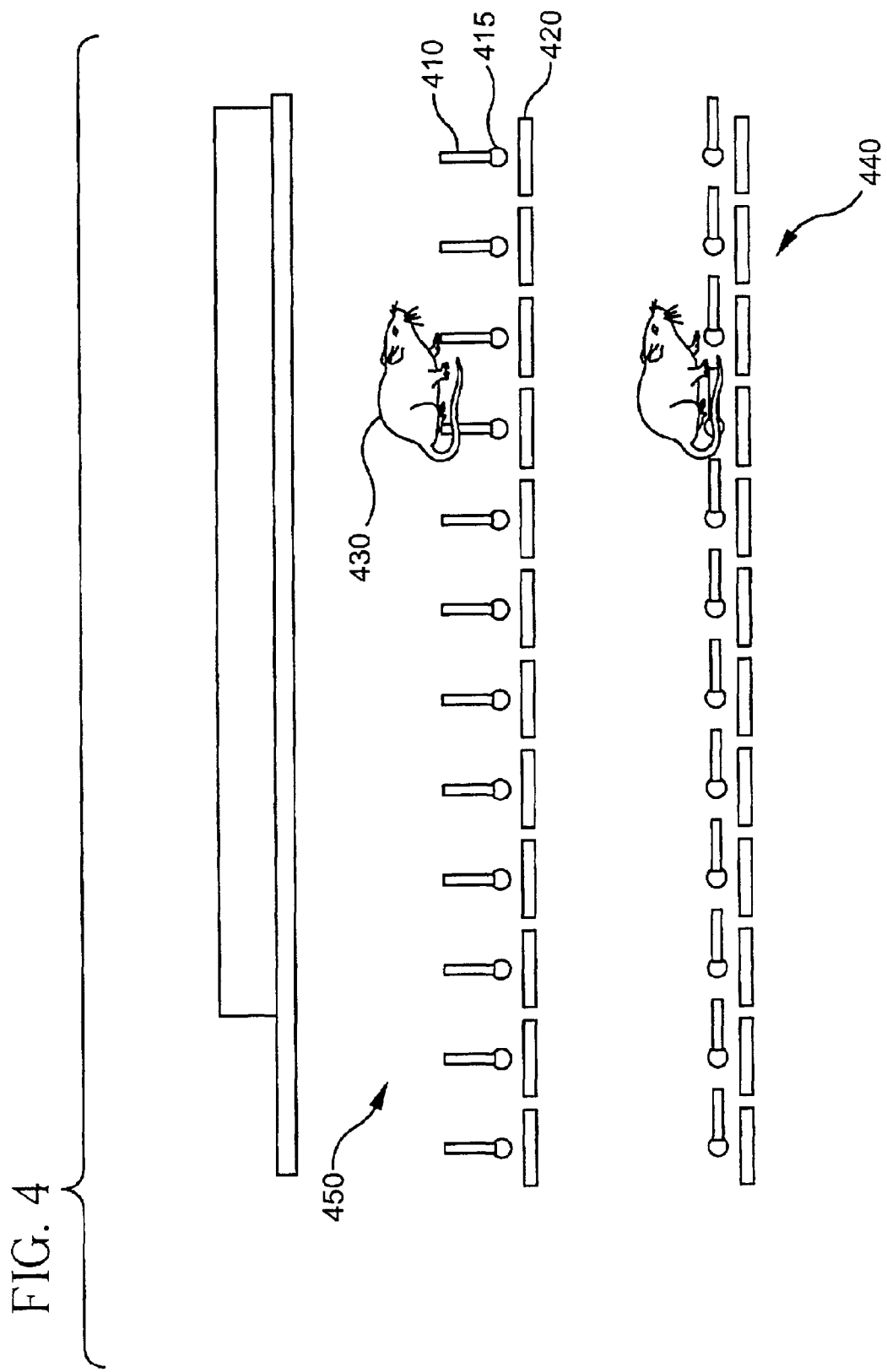
FIG. 4 is a side view of another flooring for the maze shown in FIG. 1.

Still another such element, shown in FIG. 4, is an adjustable stilt. Such stilts rotate about an axis such as a hinge and may be positioned to be parallel with the floor of the enclosure, perpendicular to the floor of the enclosure, or at any angle inbetween. When parallel to the enclosure floor, stilts act as passageways. When positioned at some other angle from the enclosure floor, the stilts act as obstacles that, depending on the angle and the training, skill, and/or dexterity of the test subject, prevent or impede passage.

Figure 5:
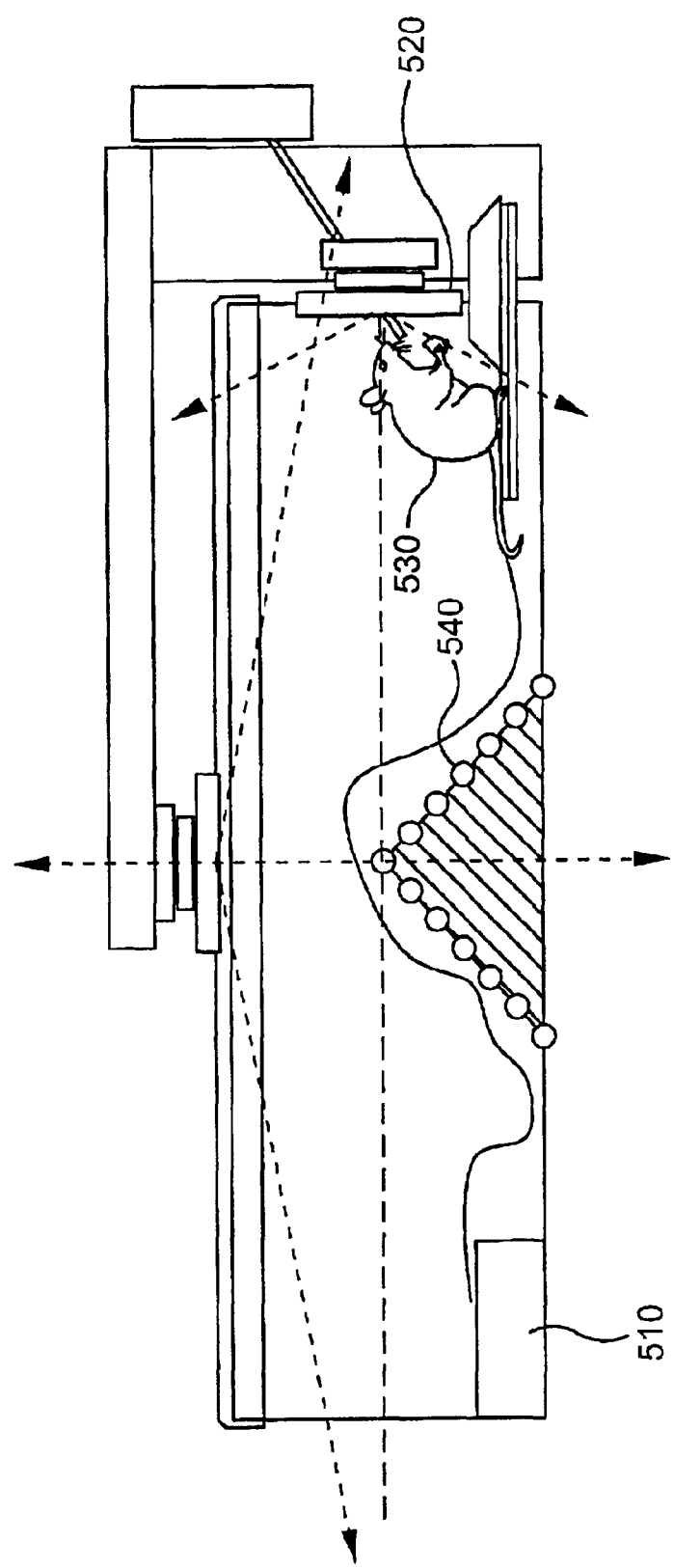
FIG. 5 is a side view of another embodiment the maze shown in FIG. 1.

A further dynamically-alterable obstacle/passageway element, shown in FIG. 5, is a block. The height of a block relative to the floor of the maze is adjustable. Like the wall element, the height of the block element may be chosen to provide an obstacle which impedes or prevents passage, or may be set to zero to provide a passageway or a portion thereof. In some embodiments, the block may be contoured or textured. Such contours and textures may include, but not be limited to, sandpaper-like surfaces, dimples, bumps, clefts, and the like.

Figure 6C:
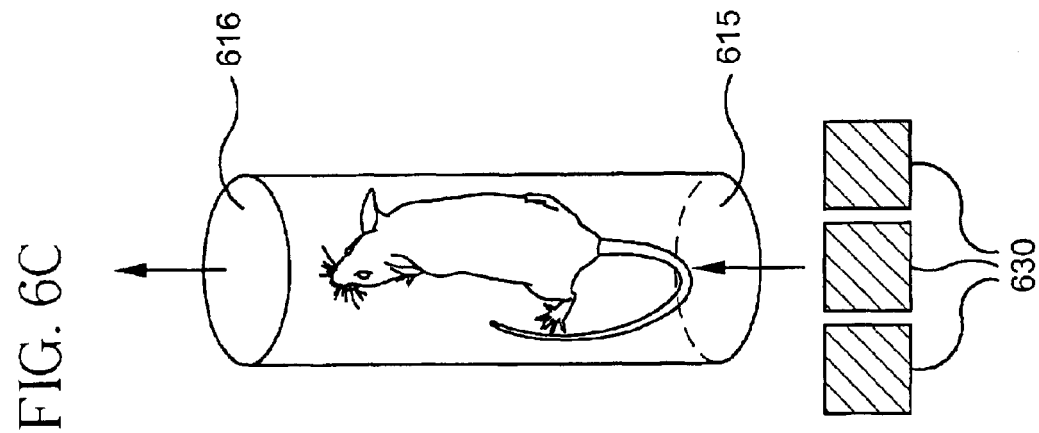
FIG. 6C is a top view of FIG. 6B.

FIG. 6 shows yet another type of obstacle called a "mouse trap". The programmable floor in this implementation may comprise of a collection of interconnected tubes through which the test subject can pass. The tubes may contain openings in close proximity with, for example, floor plates of the type described above. These openings and the corresponding floor plates can be set to be closed or open. When the tube is closed the test subject may be trapped in the tube with only one direction to traverse.

As described in detail herein, certain embodiments of the invention provide an automated control system, comprising a processor and memory device, that controls maze configuration by manipulation of obstacle/passageway elements. The configuration of the maze may be stored in the memory device and retrieved by the processor and the configuration may also be readily changed by the processor or manually programmed by the user.

The change of the configuration of the maze may be triggered by a plurality of mechanisms. The design may be arbitrarily changed by the user who can instruct the control system to change the design of the maze to a desired configuration. Configurations may be selected from designs stored in the memory of the device. In another embodiment, the change of maze design is determined based on the activity of the test subject. For example, the maze configuration may be changed based on the number of times the test subject makes contact with the obstacles in the maze. In this embodiment, the maze may increase or decrease in difficulty depending upon the test subject's success in traversing the maze and the goals of the investigator.

In another embodiment, memory devices record the number of times the test subject makes contact with the obstacles. A high number may indicate that the maze may be too difficult for the animal test subject to traverse. Accordingly, there may be a collection of values stored in the memory of the automated control system to be used as thresholds for triggering a change in the maze configuration. Once a threshold value is matched by the animal test subject, the automated control system may be triggered to reconfigure the maze so that it can be more easily traversed. Similarly, electric discharge given off by the plates in the flooring can be increased or decreased depending on the test subjects ability to traverse the maze. Alternatively, the maze may be reconfigured to be more difficult, if for example, the test subject has successfully solved the maze. By being able to alter the maze configurations due to the dynamic nature of the passageways and obstacles, the investigator can easily manipulate and change the paradigms under investigation.

The maze devices of this invention may comprise one or more sensors installed on the walls or inside the enclosure to monitor the behavior and status of the test subject. These devices may include visual sensors such as video cameras to monitor the activity of the animal test subject, heat sensors such as temperature probes to monitor the internal body temperature of the animal test subject, mass sensors such as weight platforms to monitor the body weight of the animal test subject, and memory devices to record, for example, the number of times the animal test subject has made contact with the obstacles in the maze. Data in these memory devices may be processed for the purpose of determining the behavior of the test subject during its attempt to traverse the maze, as well as determining when to reconfigure the maze and the complexity of the maze.

Figure 1:
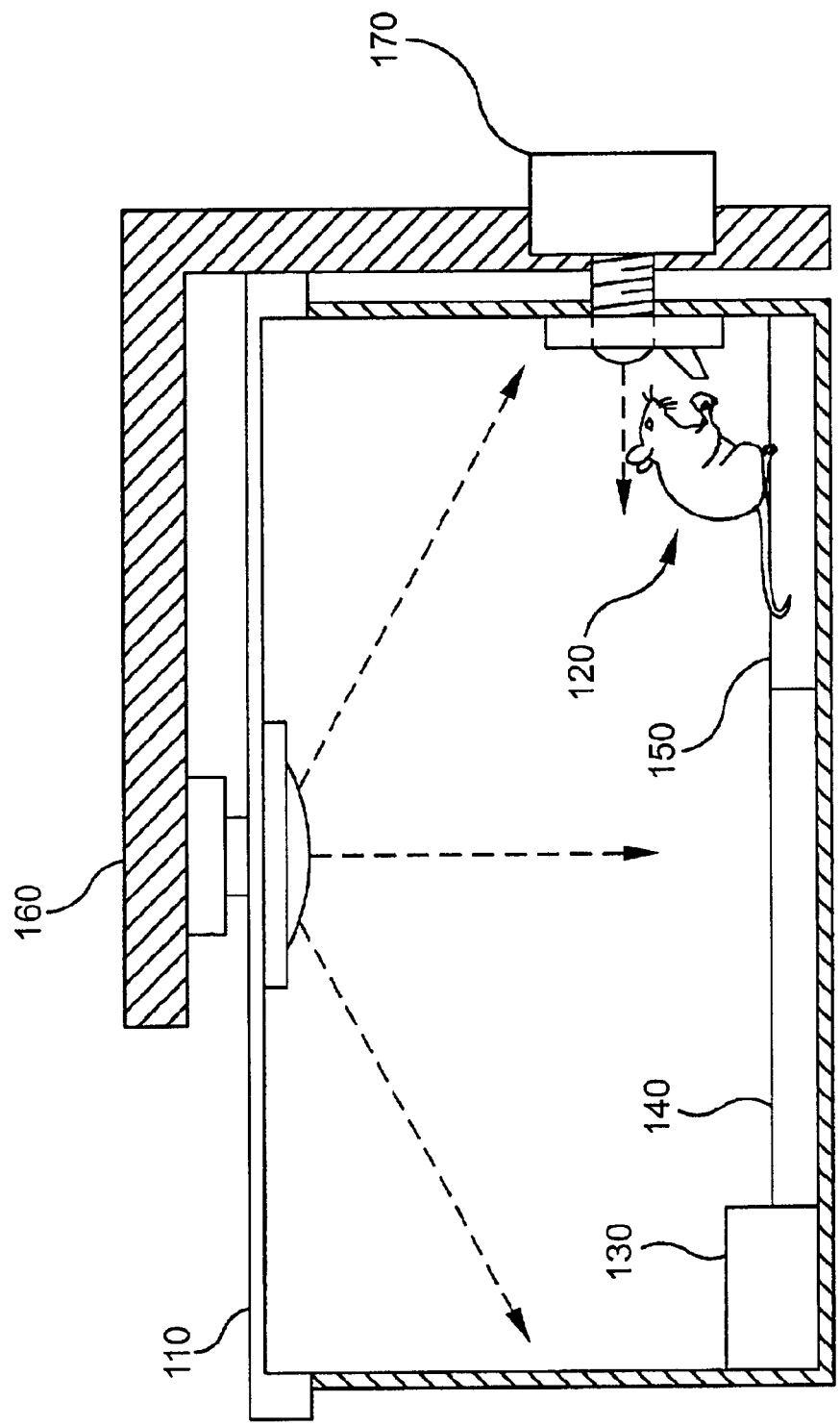
FIG. 1 is a side view of an electronic programmable maze.

FIG. 1 illustrates one implementation of the electronic programmable maze. Included in the maze is an enclosure 110, a maze floor 140, and optional means 160 for monitoring test subject 170.

Enclosure 110 provides a secure environment for the animal test subject 120. The test subject 120, depicted in FIG. 1 as a mouse, may include for example, any laboratory animal or test subject including a human. The maze shown in FIG. 1 comprises a starting point 130, depicted in the figure as a nesting area, a programmable floor 140 comprising various obstacles and possibly passageways, and an ending point 150, depicted in the figure as a food and water area. During the process to test the cognitive and/or physical abilities of the animal test subject, the animal test subject 120 is first placed in the nesting area 130. The test subject is allowed to attempt to traverse the programmable floor to reach the food and water area 150 or other type of reward. The food is placed at the ending point of the maze so to attract the animal test subject 120 to successfully traverse the maze. In order to observe and record the activities of the animal test subject 120 during its attempt, cameras 160 and 170 are installed on the side and top of the enclosure 100, providing a top view and a side view of the experiment. Other sensors and monitoring devices may also be used and will be discussed below in other embodiments.

Referring now to FIG. 2A, there is depicted one implementation of the dynamic maze. Similar to the maze mentioned previously, the maze depicted in FIG. 2A comprises a nesting area 210, a programmable floor 215 and a food and water area 250 for the animal test subject 260 to traverse. The programmable floor, in this embodiment, comprises an array of floor plates. Each of these floor plates may or may not have a light source and electrical current source that are capable of being electronically controlled to be on or off. When both the light source and the electrical current source are off, the floor plate in this state is represented by element 220 in FIG. 2. This state represents a safe passageway through the maze for the test subject that would allow the test subject to traverse from the starting point to the end point of the maze. When both the light source and the electrical current source are on, the floor plate in this state is represented by element 230. This state represents an obstacle in the maze for the test subject in which a stimulus may or may not be provided to the test subject to deter the test subject from proceeding any further toward or on the obstacle. When the light source is off and the electrical current source is on, the floor plate in this state is represented by element 240 in the figure. Alternatively the light source may be on without electric current. Any combination or configuration described above with the floor plates can be utilized in the maze. For example, the maze may contain no light indicators for the floor plates. Thus, the test subject may have no visual indication of the obstacle. In another variant, the test subject may have light or other visual indicators for some obstacles in the maze and no visual indicators for other obstacles. In still another variant, the test subject may have only visual indicators for obstacles and no stimulus applied when traversing over an obstacle. In a further embodiment the visual indicator may define a different path than that defined by the configuration of pathways and obstacles. These examples are only given as illustrative examples of the programmable maze and are not intended to be exhaustive and limit the device to only these embodiments.

Depending on the implementation, when the floor plate has the electrical current source on as in elements 230 and 240, it is electrically charged. The electrically charged floor plates constitute obstacles in the maze by administering an electrical shock to the animal test subject 260. Depending on the strength of the shock, the test subject may be prevented from or impeded in traversing the electrically charged floor plate. Although the electrical shock administered to the animal test subject 260 should be strong enough deter the animal, it should generally not be strong enough to harm or incapacitate the animal. Also both floor plates 230 and 240 are obstacles in the programmable floor, despite the fact that the light source is on in plate 230 but off in plate 240. In this implementation, the floor plates 220 that have neither the light source nor the electrical current source powered constitute a passageway through the maze. Thus by turning on and off the various light sources and electrical current sources in the various floor plates, various design configurations of the maze can be established. In effect, a different maze can be set in place by simply turning on and off the various light sources and various electrical current sources.

It is stressed that although in this embodiment an electrical current source is used to deter the animal test subject 260, various other devices may be used in its place to achieve the same objective without diverting from the spirit of the present invention. One possible device in place of the electrical current source may be a sound source, which can produce a sound alarm when the animal test subject 260 comes in contact with the floor plate that may or may not contain the sound source. Yet another possible device is another light source, which can emit a flash of light when the animal test subject 260 comes in contact with the floor plate containing the light source. In addition, in place of the electric current, a heat or cold source in the floor plates may be turned on or off and used as an obstacle in the maze. Vibration energy or motion in the floor plates may also be used in addition to any combination of the previously mentioned mechanisms in the floor plates. The floor plates described may be individually disposed or composed of a single flooring depending on the result sought.

Figure 2B:
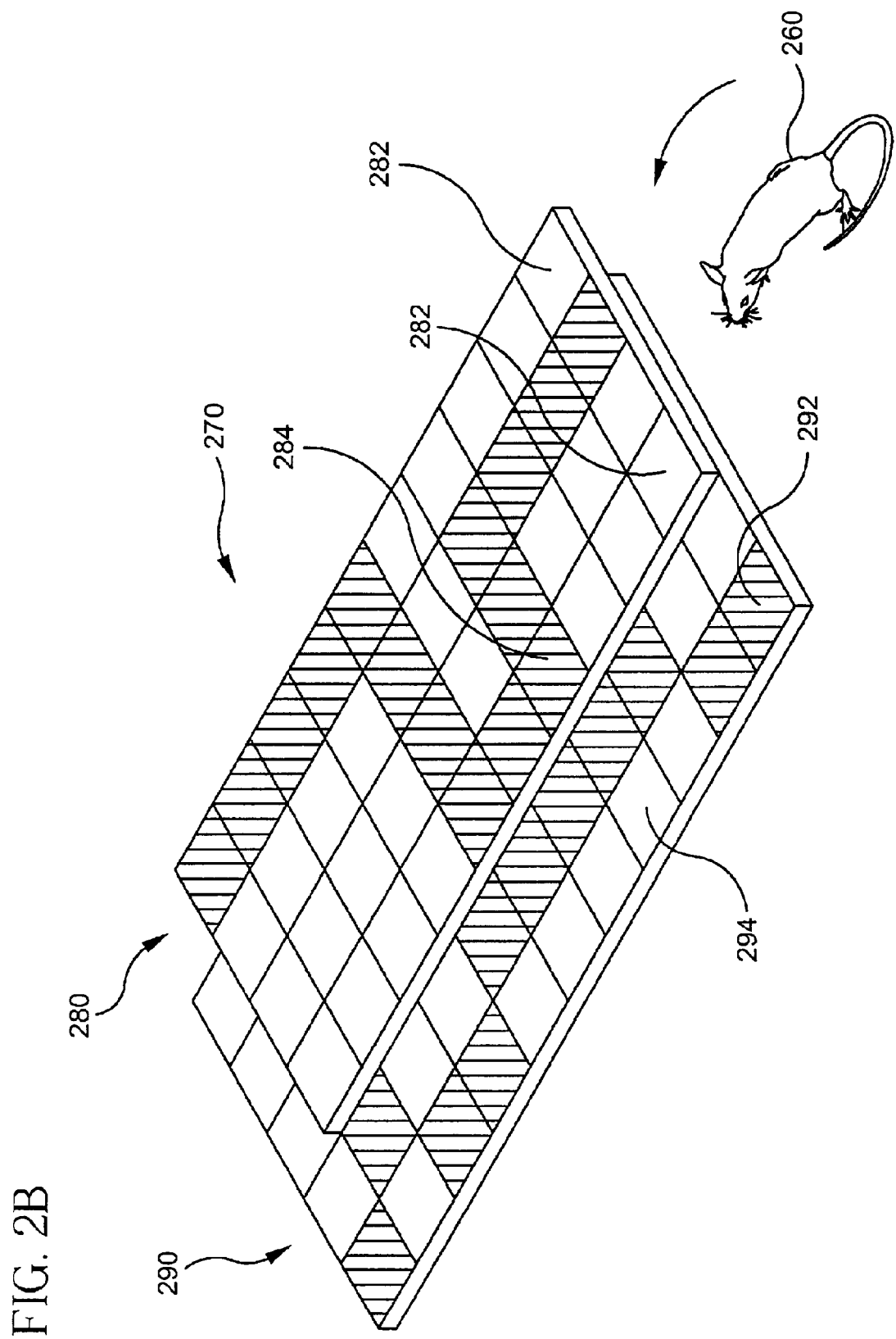
FIG. 2B is a perspective view of multiple floors for the maze of FIG. 1.

In yet another embodiment, shown in FIG. 2B, a device 270 further comprises a secondary stimulus device 290 which reinforces or conflicts with that pathway of the maze defined by the configuration of passageways 282 and obstacles 284. For example, a programmable panel of light pads 292 and 294 may be situated below the dynamic layer 280 comprising the passageways 282 and obstacles 284. Light pads may then be illuminated so that they reinforce (e.g., parallel), or conflict (e.g., define a path different from that which leads to the end of the maze) with the passageway that leads to the maze endpoint. Alternate embodiments within the scope of this invention may include placing the secondary stimulus in a different orientation such as above or at the side of the test subject 260.

Figure 2C:
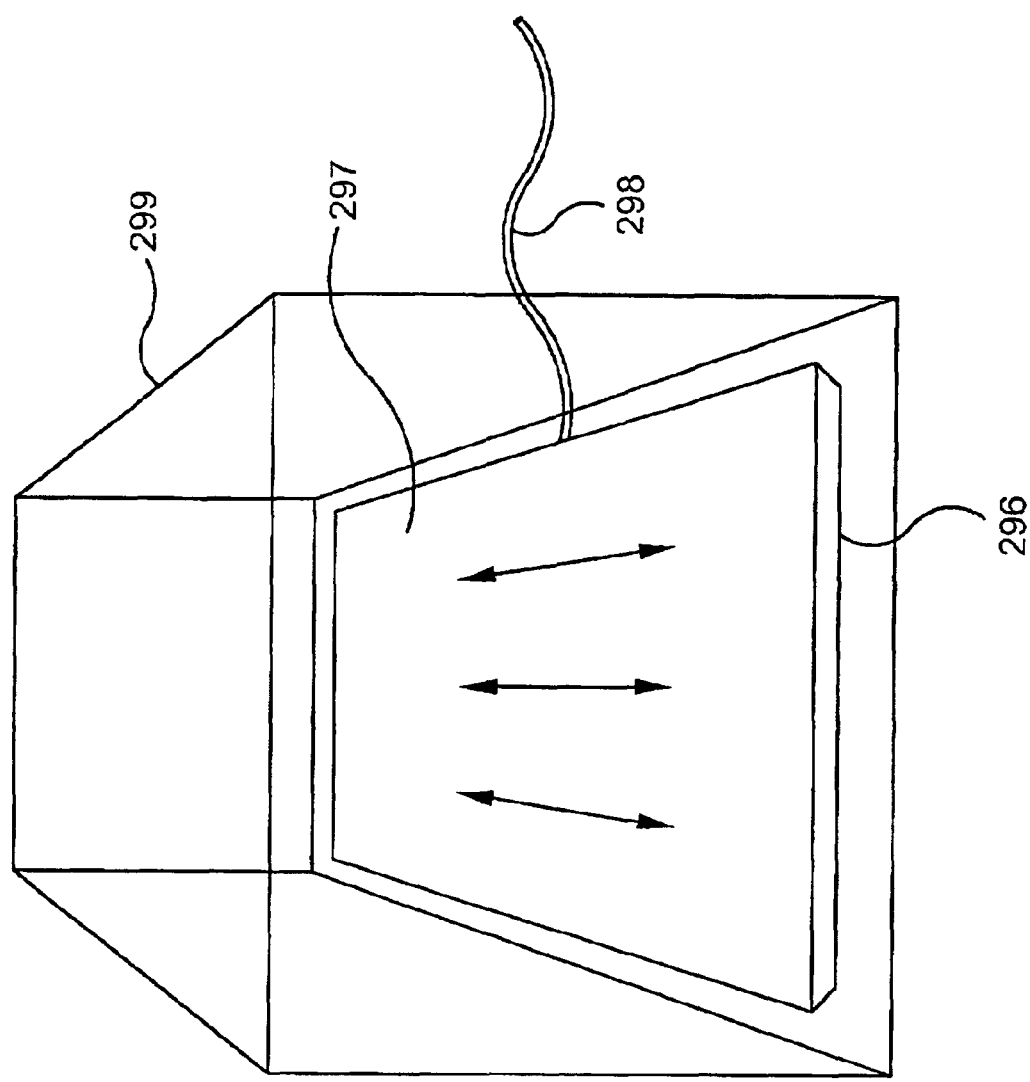
FIG. 2C is a perspective view of a vibrating floor for the maze of FIG. 1.

FIG. 2C illustrates an example of flooring using vibration energy or motion in the flooring and/or floor plates. Animals perceive low frequency vibrations and movements of the substrate very accurately and react strongly with arousal and defensive mechanisms. One way to stimulate a test subject such as a mouse (or small mammal) is to produce such vibration or movement of the substrate on which it rests. A floor insert 296 may be used to accomplish such a function. In one embodiment, floor insert 296 comprises a floor 297 (either soft and flexible or rigid) that is attached to an actuator (not shown) that vibrates or moves in a certain direction or multiple directions at high or variable speeds. The actuator may be disposed within the floor insert 296 or outside of the floor insert 296. Control of the floor insert 296 may be done by a vibration adjustment mechanism (also not shown) that may be controlled inside or outside the floor insert 296. An example of controlling the floor insert 296 outside the floor insert 296 is shown in FIG. 2C using a cable 298.

A short period of activation of the floor insert 296 may result in a startle response, whereas longer period will constitute stressful stimulation. The floor insert 296 may be composed of individual floor plates that vibrate independently of each other thereby giving motion to portions of the floor while portions of the floor remain still or may be composed of a single flooring that vibrates as illustrated in FIG. 2C. A housing 299 may be used to encase the test subject and provide a testing environment where the floor insert 296 may be placed. The floor may vibrate independent to or in response to the test subject traversing the maze. Any of the above embodiments and any embodiments discussed herein may be used in any combination or individually to achieve the desired result sought by the user of the programmable maze. The above embodiments provide a home cage environment or holding and measuring apparatus that provides rapid re-configuration for the measurement of different behavioral responses.

Figure 3A:
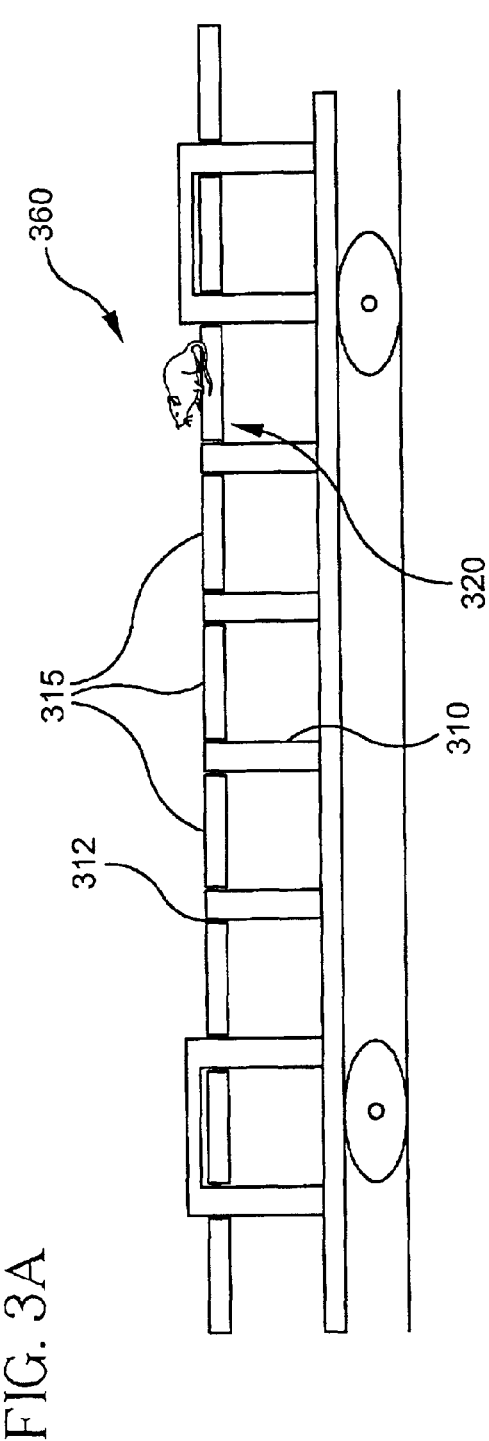
FIG. 3A is a side view of flooring in the down state for the maze shown in FIG. 1.
Figure 3B:
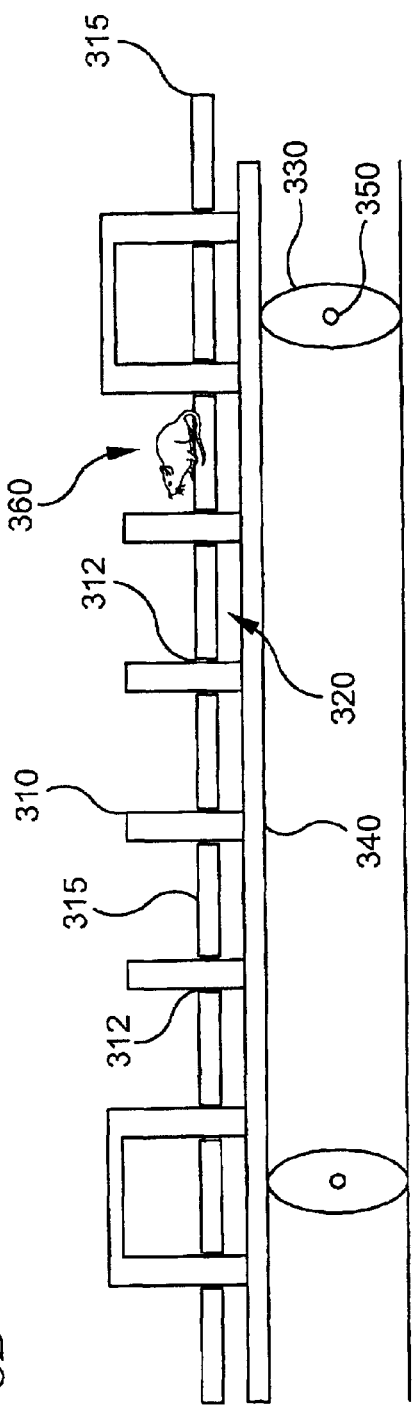
FIG. 3B is a side view of flooring in the up state for the maze shown in FIG. 1.

Adverting to FIGS. 3A and 3B, there is illustrated another obstacle that may be used in the programmable maze. Similar to the embodiment depicted in FIG. 2A, in this embodiment there is also an endpoint, such as for example a nesting area and a food and water area, although they are not shown in the figure. The programmable floor in this embodiment comprises a number of various physical obstacles, such as wall 310, that are attached to a number of movable plates 315 that form a collapsible floor 320. The movable plates are capable of moving in the vertical direction by mechanism 330, which is capable of raising or lowering the movable plates 315 as the mechanism 330 rotates about the axis 350. The moveable plates may move in any sequence, either uniformly or individually depending on the needs of the user. The movement of the collapsible floor 320 can be controlled by the user either manually or through a program preinstalled and adapted to the specific experiment being conducted.

Depending on the implementation, the flooring may include a secondary floor 340 built below the movable floor 320 such that the walls 310 fit through several openings 312 that correspond to the physical obstructions or walls 310 when the collapsible floor is activated. It is understood that flooring 320 may be held stationary and flooring 340 moved or vice versa in order to create the collapsible floor effect. Similarly, both flooring 320 and flooring 340 may move to create the collapse floor effect and produce wall 310 as an obstacle in the maze. When the movable plates 315 are in their uppermost position, the physical obstructions attached to them protrude out above the stationary floor, thereby constituting the obstacles for the maze, as depicted in the FIG. 3B. The rotation mechanisms 330 are in the "up" state, thus providing the animal test subject 360 with obstacles. When the movable plates 320 are in their bottommost position, the physical obstructions attached to them are flush with the stationary floor, thereby filling in the number of openings in the stationary floor, as depicted in FIG. 3B. The rotation mechanisms 330 are in the "down" state, thus providing the animal test subject 360 with passageways. Although FIGS. 3A and 3B only depict the movable plates moving in unison, each moveable plate may move individually by incorporating individual rotation mechanisms 330 on each plate. Movable plates 315 and different combinations of the movable plates 315 with walls 310 in "up" and "down" states define different design configurations of the maze.

In certain embodiments, states between "up" and "down" may be possible whereby one may effectively choose the height to which a wall rises. In such embodiments, by setting the height such that the test subject is incapable of climbing the wall, an obstacle that prevents passage may be formed. By setting the height such that the test subject is, perhaps with effort, capable of climbing the wall, an obstacle that impedes passage may be formed. By setting the wall to not rise from the floor, a passageway or portion thereof may be formed.

FIG. 4 depicts another implementation for obstacles in the dynamic maze. The programmable floor shown in FIG. 4 comprises an array of stilts 410 that are attached to a stationary floor 420 with a corresponding array of hinges 415. These hinges 415 allow the stilts 410 to be positioned parallel to the stationary floor as shown in diagram 440, perpendicular to the stationary floor as shown in diagram 450, or at any other angle desired. The position angle may be set either manually by a user or automatically by a program. In some embodiments, when the stilts are in a position other than the parallel position, the stilts may, depending on the angle selected, act either as obstacles that prevent or obstacles which impede passage of test subject 430. When the stilts are in the parallel position, the stilts are not obstacles but passageways for the animal test subject 430 in the maze. Thus by choosing various numbers of stilts and the angle at which they are angled from the surface, different design configurations of the maze having different degrees of difficulty can be achieved.

Referring now to FIG. 5, there is depicted still another implementation of the dynamic maze. Similar to the implementation depicted in FIG. 2A, in this implementation there are also a nesting area 510 and a food and water area 520. The programmable floor in this embodiment comprises a block 540 that can be programmed to move to various elevations when designated as obstacles, as shown in FIG. 5. In one embodiment, the block 540 moves uniformly in a vertically motion up and down. In another embodiment, the block 540 is configured as steps that may or may not move in concert with each other. Thus, various steps may move and some may remain still or all steps may move but at various times at different sequences or all the steps may move in concert with each other. The maze may be composed of only one obstacle as shown in FIG. 5 or preferable more than one and most preferably at least two obstacles. Generally, blocks 540 that are designated as obstacles that have a higher elevation than blocks that are not designated as obstacles. Blocks whose height is such that test subjects cannot climb over them may create obstacles that prevent passage. Elevated blocks that the test subject can climb over may constitute obstacles that impede passage. Lower elevation blocks constitute the passageways of the maze. Thus by designating various blocks as obstacles or pathways, different design configuration of the maze can be achieved. Again, the obstacles may or may not respond to the test subject traversing the maze depending on the results sought. In addition, the obstacles can be used in the maze with any combination of other obstacles described herein or known by those skilled in the art and/or used individually. Again, the maze provides an environment that provides rapid reconfiguration for the measurement of different behavioral responses without intervention from the user.

In FIG. 5 as well as the other embodiments discusses herein, there may be a number of monitoring devices installed in the programmable maze. Devices such as temperature probes, weight platforms and video cameras and the like may all be utilized in the maze to monitor the test subject as it traverses through thee maze. In addition, infra red and ultrasonic position detectors may be used. Sensor pads may also be used as a means of detecting the location of the mouse by measuring the electrical signals injected into a pad by the test subject, such as a mouse for example, when the test subject comes in contact with the pad. The signals are analogous to the signals detected by electrical pads attached to human subjects during ECG measurements. In this invention the signals are used to determine the location of the mouse by identifying the physical pad at which the signal is present. The signal, after suitable amplification and filtering, may further be used to determine the anxiety level of the subject by measuring its periodicity, essentially the heart rate of the mouse. This in turn may be used as a determinant in increasing/decreasing the complexity level of the maze. These monitoring devices may be used in any of the previous implementations described above as well.

FIG. 6 illustrates the dynamic programmable maze with yet another type of obstacle called a "mouse trap". The programmable floor in this implementation may comprise a collection of interconnected tubes 610 through which the test subject can pass. Alternatively, the tubes may be unrelated to each other or there may be only one tube utilized in the maze. The tube may or may not be used in the maze in conjunction with any of the previous obstacles described depending on the implementation. Similarly, any of the obstacles described herein may or may not be used in the maze in combination with other types of obstacles depending on the needs of the user and testing required. In one embodiment, obstacles may be used as movable barriers between interconnected tubes. In a "mouse trap" obstacle implementation, the test subject is released into the tube 610. The tube 610 itself may or may not be dynamic in the sense that it may or may not be able to be programmed to embody different mazes. The programmable aspect of this implementation may include a number of openings 615, 616 in the tubes 610. In close proximity with these openings are floor plates 630, with each floor plate optionally having an electrical current source and/or light source and/or any of the implementations previously described. These openings and the corresponding floor plates 630 can be programmed to either close or open. When the tube is activated to be closed, the test subject is trapped in the tube with only one direction to traverse. For example, when an opening is designated as closed, the floor plate 630 correspondingly has its electrical current source turned on. The floor plate 630 will administer an electric shock to the animal test subject 620 when the animal comes in contact with floor plate, therefore deterring the animal test subject 620 from exiting the tubes 610 through an opening that is designated as closed. When an opening is designated as a starting point, the electrical current source of the corresponding floor plate 630 is initially turned off, and will be turned on only after the animal test subject 620 enters the tube 610. Therefore, the test subject is prevented from exiting the opening designated as the starting point. When an opening is designated as the ending point, the electrical current source of the corresponding floor plate 630 is turned off during the entire time in which the animal test subject 620 is attempting to traverse the maze. A plurality of tubes may be used to create the obstacles in the maze.

Figure 6A:
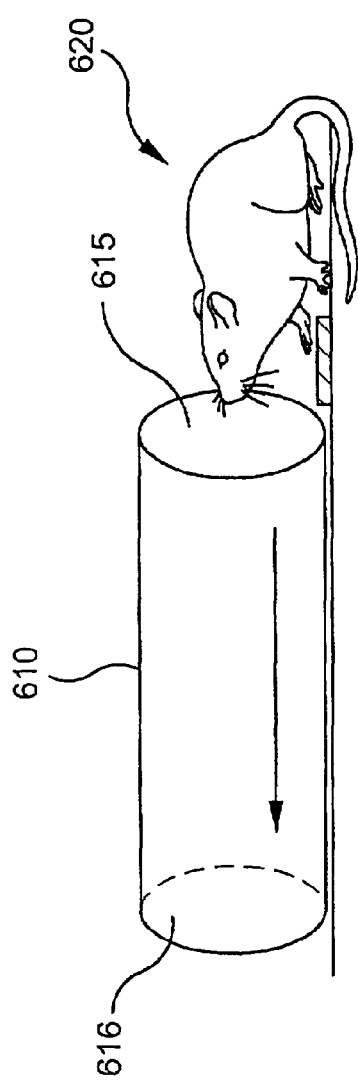
FIG. 6A is a side view of an obstacle that may be utilized in the maze of FIG. 1.
Figure 6B:
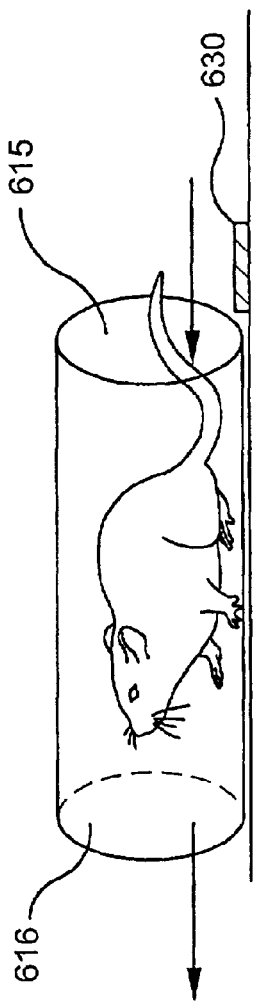
FIG. 6B is a side view of the obstacle in FIG. 6A illustrating use by a test subject.

Although the floor plates 630 depicted in FIGS. 6A and 6B use electric shock to prevent the animal test subject 620 from traversing, the opening may utilize other means of deterrent, such as a sound alarm or a flash of light when the animal test subject 620 comes in contact with the floor plate or any number of deterrents can be used instead of electric shock or physical barrier without moving away from the spirit of the invention. By designating various openings as opened or closed, or starting points and ending points, various design configuration of the maze can be achieved.

Figure 7:
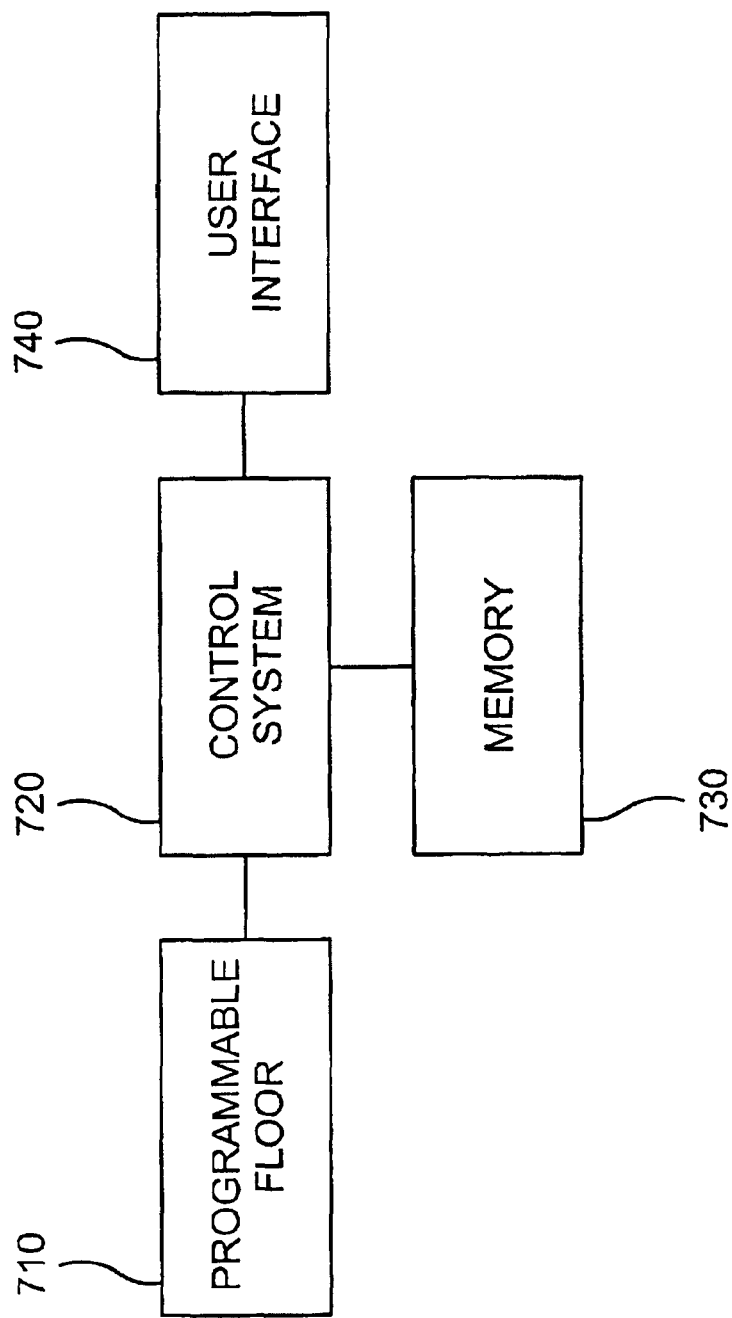
FIG. 7 is a block diagram depicting a control system that allows the user to program the programmable floor.

The programmable floor of the dynamic maze in these various embodiments can be programmed via several methods. Referring now to FIG. 7, there is depicted a block diagram for a system that allows a user to program the maze. There is typically a control system 720 in communication with the programmable floor 710, where the control system 720 is capable of sending signals to the programmable floor 710 to turn on or off various obstacles such as physical barriers, light sources or electrical current sources in various floor plates. Elements of the programmable floor 710, depending on the implementation, may include any of the previous obstacles described either individually or in any combination. The instruction from the user is input into the user interface 740, and the same user interface 740 relays the instructions to the control system 720. Depending on the implementation, the user interface may also be the control system. In one mode of operation of the control system, the user specifies which devices or elements of the programmable floor are to be designated as obstacles, thereby constructing an arbitrarily designed maze. In another mode of operation, the user may choose one design configuration of the maze from a number of different design configurations stored in memory 730, which is in communication which the control system 720.

Depending on the implementation, other methods can be utilized to program the programmable maze. In one implementation, an automated control system that reprograms the programmable floor in accordance with the number of times the animal test subject makes contact with the obstacles in the maze. For example, during drug experimentation, an experimental drug may impair the cognitive and physical abilities of the animal test subject to the point that it cannot successfully traverse some of the more difficult mazes. With traditional static mazes it may be difficult to discern differences in impairment of physical versus cognitive ability. By providing dynamic mazes which may be altered without removing the test subject, an investigator can readily test an animal's ability to solve mazes of different complexity requiring similar physical ability, thus providing a means for assessing cognitive ability with minimum interference due to physical impairment. Therefore, the difficulty of the maze that is successfully traversed by the animal test subject may be used as an indication of the effect the drug had on the cognitive abilities of the animal test subject. An efficient method to determine the most difficult maze that can be traversed by the animal test subject under the influence of an experimental drug is depicted in FIGS. 8 and 9.

Figure 8:
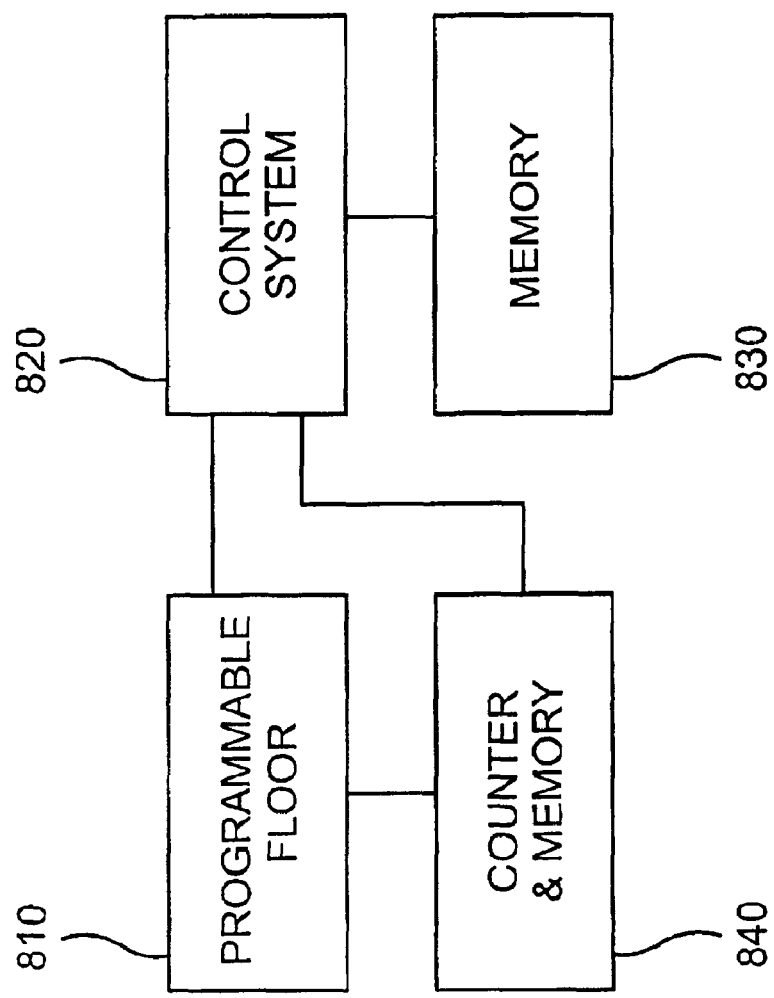
FIG. 8 is a block diagram depicting an automated control system that programs the programmable floor.
Figure 9:
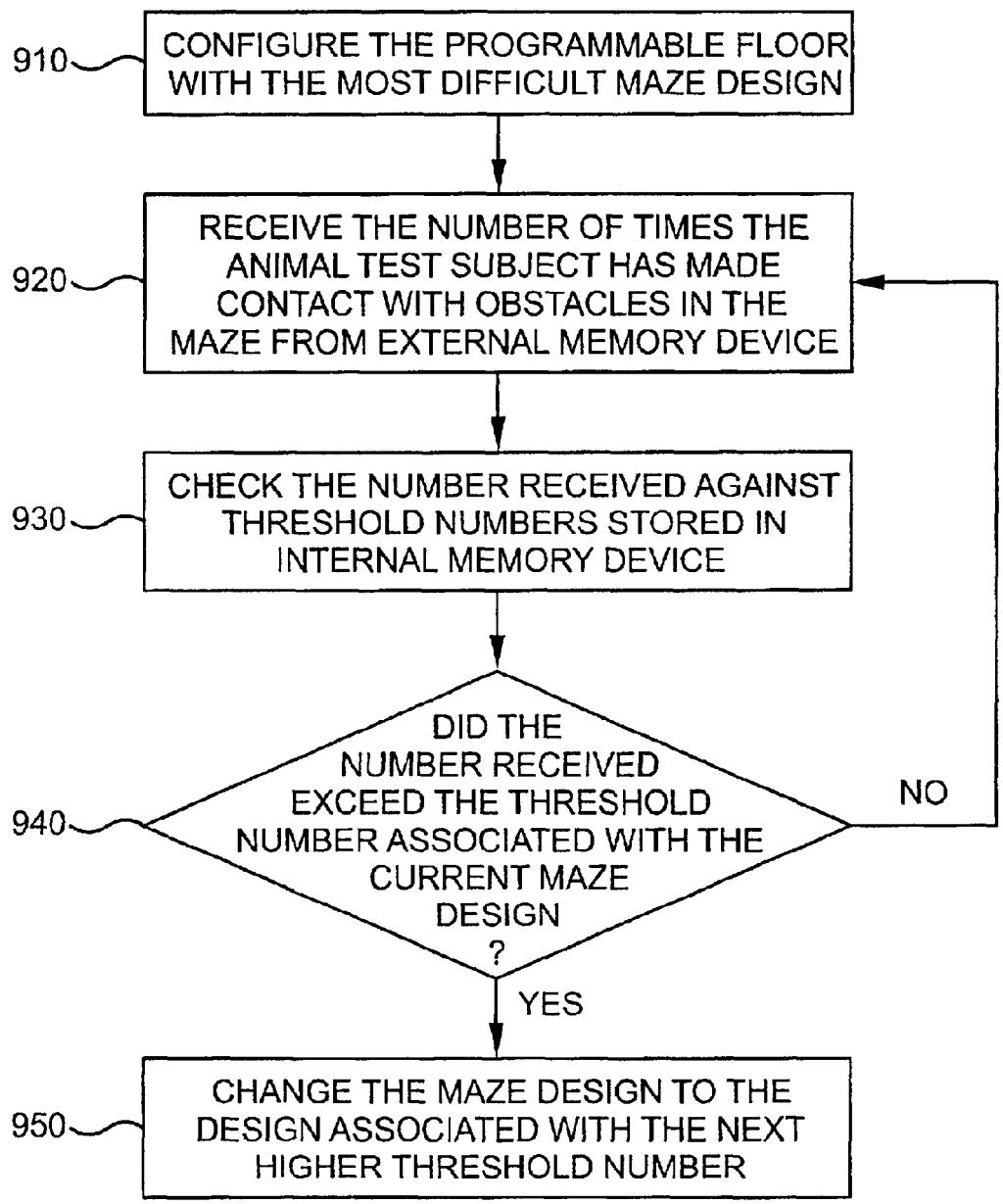
FIG. 9 is a flowchart depicting the operation of the automated control system presented in FIG. 8.

FIGS. 8 and 9 represent diagrams for one implementation of such an automated control system, with the flow chart in FIG. 9 showing a possible embodiment of system operation. The automated control system 820 is in communication with the programmable floor 810. In one variant, control system 820 configures the programmable floor with the most difficult maze design stored in memory, as shown in step 910. A counter and memory device that is in communication with the programmable floor and has sensors in the obstacles in the maze may detect the number of the times the animal test subject makes contact with the obstacles, i.e. running into the obstacles or grazing the side of the obstacles. The sensors transmit this data continuously to the control system 820. The control system 820 then receives the data in step 920. A good indicator of the animal test subject's inability to traverse the maze is the number of times it makes contact with the maze. If the number of times exceeds a certain predetermined number, then a simpler maze may be presented to the animal test subject automatically through the logic in the control system. The automated control system 820 accomplishes this task in step 930.

By comparing the data received from counter and memory 840 with the data stored in memory 830 which provide threshold levels, the automated control system 820 determines in step 940 whether the data from the trial exceeds the first of the predetermined threshold data. If the threshold is exceeded, then the automated control system 820 reprograms the programmable floor 810 with a second or simpler configuration, in this example, of maze design stored in memory. If the threshold is not exceeded, the automated control system 820 continues to receive data from the counter and memory 840. This process is repeated until the animal test subject successfully traverses the maze or the programmable floor is programmed with the simplest maze design configuration. In a similar manner, the automated control system could reprogram the programmable floor 810 with a more difficult configuration in the case where a test subject completed the maze in an amount of time that fell below a chosen threshold.

Figure 10:
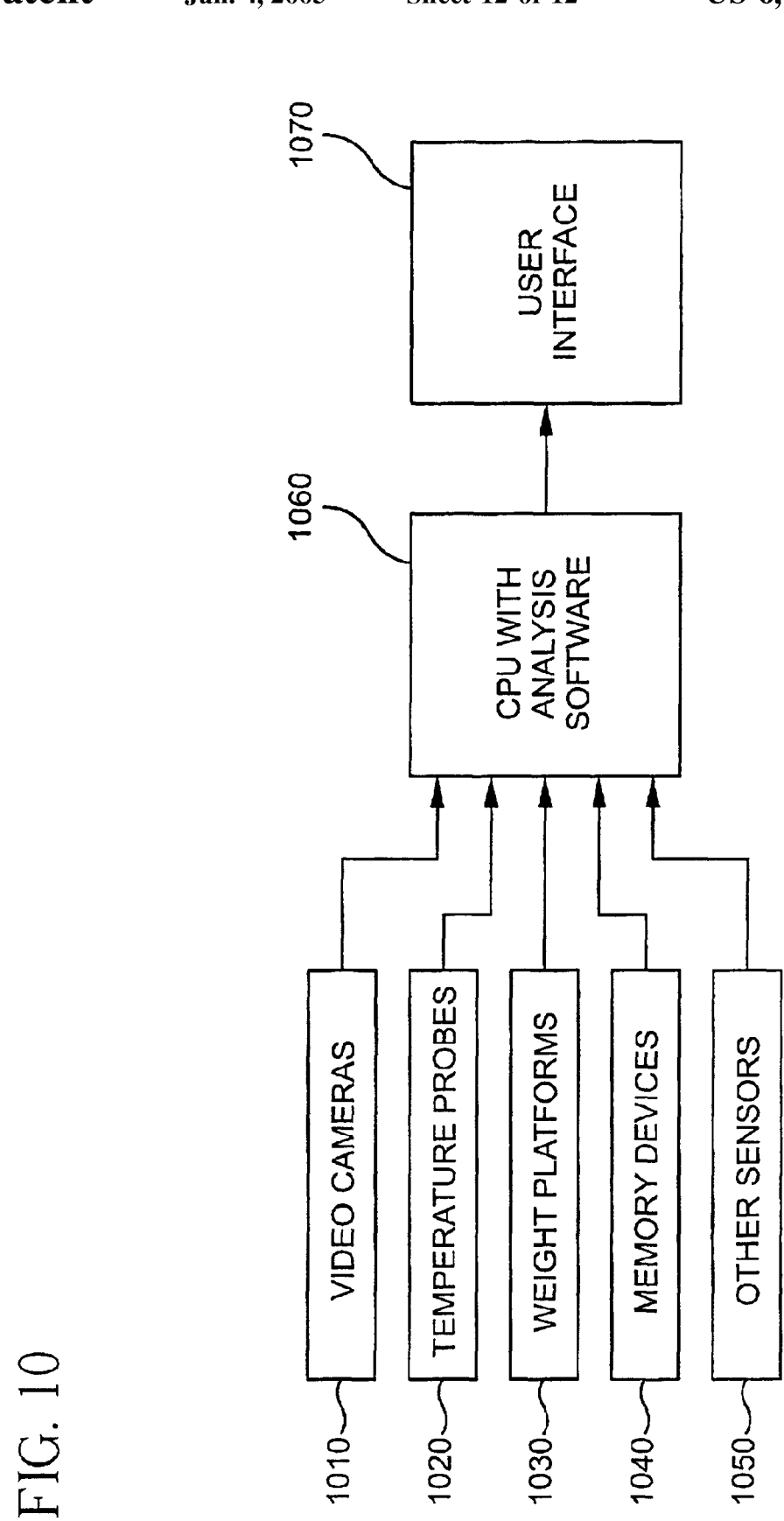
FIG. 10 is a block diagram depicting a system that determines the physical and mental condition of the animal test subject by analyzing various data from monitoring devices.

As shown in FIG. 10, it is within the scope of the invention to collect data, such as the amount of time it takes the subject to reach the end of a maze, using various monitoring devices. Such devices includes, but are not limited to, video cameras 1010, temperature probes 1020, weight platforms 1030, memory devices that record the number of times the animal test subject makes contact with obstacles 1040, and other sensors 1050. Other sensors include, but are not limited to infra red and ultrasonic position detectors for example. As previously stated, sensor pads may also be used as a means of detecting the location of the mouse by measuring the electrical signals injected into a pad by the test subject, such as a mouse for example, when the test subject comes in contact with the pad. The signals are analogous to the signals detected by electrical pads attached to human subjects during ECG measurements. In this invention the signals are used to determine the location of the mouse by identifying the physical pad at which the signal is present. The signal, after suitable amplification and filtering, may further be used to determine the anxiety level of the subject by measuring its periodicity, essentially the heart rate of the mouse. This in turn may be used as a determinant in increasing/decreasing the complexity level of the maze. These monitoring devices may be used in any of the implementations described herein. Data is feed into a computer or other logic 1060 for analysis of the physical and mental condition of the animal test subject. The results of the computer analysis can be received through a user interface 1070.

In certain embodiments, the logic of elements 720, 730, 740, 820, 830, 840, 1060, and 1070 of the systems of FIGS. 7, 8, and 10 may be implemented using a general purpose computer such as, for example, a Dell Optiplex running Linux or Windows XP or a Macintosh G4 running Linux or OS X. The general purpose computer may connect to sensors 1010–1050 using an industry-standard interfaces such as EIA-232 serial, Universal Serial Bus (USB), IEEE 1394, IEEE 802.11, or PCI. The general purpose computer may be designed to interface with the devices which perform the actual manipulation of obstacle/pathway elements. For example, the general purpose computer may use an analog/digital interface on a PCI card to connect to the motors of obstacle elements, such as those that rotate the stilt elements about their axes. In alternate embodiments, the logic of elements 720, 730, 740, 820, 830, 840, 1060, and 1070 of the systems of FIGS. 7, 8, and 10 may be implemented using custom circuitry In another embodiment, the maze can be coupled to a database system that provides the generation, acquisition, and maintenance of databases of relevant behavioral models that can be used for database mining purposes. For example, associations, patterns, and trends of drug responses or genetic manipulations to the test subject can be discovered. In addition, information about the drug effects and/or genetic manipulation may be classified and predictive models may be provided. The maze may provide automated testing using hardware and software to permit collection of behavioral data on a test subject traversing the maze. The maze provides the flexibility to be used independently as well as used in conjunction with other test devices or systems. For example, the maze may be used in conjunction with other test devices currently available or in development. The automated systems contained in the dynamic maze provides a more cost-efficient, user-independent, tool for drug and genetic research.

The operation of user interfaces 740 and 1070, control systems 720 and 820, the analysis software of 1060, and counter 840 may be implemented as software running on the general purpose computer. Such software may be programmed in a language such as Java, Objective-C, C, or C++ to provide the functionality described herein, such as that shown in the flow chart of FIG. 9. The operation of user interfaces 740 and 1070 may be implemented, for example, by having the software interface with APIs and/or frameworks provided by the operating system for presenting data to the user and receiving input from a user. The operation of control systems 720 and 820 may be implemented, for example, by having the software, using existing or custom APIs and/or frameworks, manipulate obstacle/pathway elements and receive input from sensors 1010–1050.

Although the invention has been described in detail in the foregoing embodiments, it is to be understood that the descriptions have been provided for purposes of illustration only and that other variations both in form and detail can be made thereupon by those skilled in the art without departing from the spirit and scope of the invention, which is defined solely by the appended claims.

Furthermore, since numerous modifications and variations will readily occur to those skilled in the art, it is not desired that the present invention be limited to the exact construction and operation illustrated. Accordingly, all suitable modifications and equivalents which may be resorted to are intended to fall within the scope of the claims.

It should be understood that the above description is only representative of illustrative examples of embodiments and implementations. For the reader's convenience, the above description has focused on a representative sample of all possible embodiments, a sample that teaches the principles of the invention. Other embodiments may result from a different combination of portions of different embodiments. The description has not attempted to exhaustively enumerate all possible variations. For example, some obstacles such as the floor plates may be incorporated with other obstacles such as the stilts. Alternatively, the obstacles may be utilized individually in the maze. Similarly, the operation of the maze may have a portion run by an automatic program and another portion of the same maze run manually. It is recognized that doing so may allow for the deletion or addition of one or more of the functions described in the block diagrams and flow chart given as examples of the operation and configuration of the programmable maze.

Alternate embodiments may not have been presented for a specific portion of the invention, and may result from a different combination of described portions, or that other undescribed alternate embodiments may be available for a portion, is not to be considered a disclaimer of those alternate embodiments. It is appreciated that many of those undescribed embodiments are within the literal scope of the following claims, and others are equivalent.

What is claimed is:

1. A dynamic maze, comprising:
   an interior maze volume defined by multiple boundary surfaces; and
   at least two removable obstacles under control of a programmable system that configures the maze by inserting or removing at least one of the at least two obstacles through a boundary surface of the maze.

2. The maze according to claim 1, further comprising:
   a logic component that configures the maze and is responsive to ability of a test subject to traverse the maze.

3. The maze according to claim 2, further comprising:
   a clock component for measuring time required by the test subject to traverse all or a portion of the maze such that the logic component receives time data for use in determining configuration of the maze.

4. The maze according to claim 1, wherein the obstacle transmits a primary stimulus to a test subject in a rewarding or noxious manner.

5. The maze according to claim 4, further comprising:
   a secondary stimulus that can reinforce or conflict with the primary stimulus.

6. The maze according to claim 1 further comprising:
   a monitor to observe behavior of a test subject.

7. The maze according to claim 6 wherein the monitor records movements of the test subject.

8. The maze according to claim 1 wherein the obstacle is configured to impede ability of a test subject to traverse said obstacle.

9. The maze according to claim 1 wherein the obstacle is configured to preclude a test subject from traversing said obstacle.

10. The maze according to claim 1, further comprising:
    a starting point and an end point.

11. The maze according to claim 10, wherein said starting point stimulates a punishment for a test subject.

12. The maze according to claim 10, wherein said end point stimulates a reward for a test subject.

13. The maze according to claim 1 further comprising flooring sensors for detecting location of a test subject.

14. The maze according to claim 1 further comprising temperature sensors for detecting ambient temperature and temperature of a test subject.

15. The maze according to claim 1 further comprising weight sensors for detecting weight of a test subject.

16. The dynamic maze according to claim 1, wherein at least two of said obstacles can be removed through one of the following: the outer walls, the floor, or the ceiling, encompassing said maze.

17. The dynamic maze according to claim 1, wherein in at least one case, removing said obstacle, positions said obstacle parallel to said floor or said ceiling.

18. A dynamic maze, comprising:
    an enclosure, for holding a test subject, defined by multiple boundary surfaces; and
    at least two removable obstacles under control of a programmable system that configures the maze by inserting or removing at least one of the at least two obstacles through a boundary surface of the maze.

19. The dynamic maze according to claim 18, wherein the enclosure is a cage suitable for housing a laboratory animal.

20. The dynamic maze according to claim 19, wherein the enclosure is portable.

21. The dynamic maze according to claim 18, wherein the maze is configured to concurrently study a plurality of test subjects.

22. The dynamic maze according to claim 18 further comprising:
    a laboratory animal test subject.

23. The dynamic maze according to claim 22, wherein the laboratory animal is a mouse.

24. The device according to claim 18 further comprising:
    raised stilts positioned to require a test subject to move from one stilt to the next.

25. The device according to claim 24 wherein at least some of the raised stilts are raised to a uniform height and angle.

26. The device according to claim 24 wherein the raised stilts are arranged relative to each other so as to cause the test subject to move by placing one foot on a first stilt and another foot on a second stilt and then move the one foot to a different stilt.

27. A dynamic maze, comprising:
    an enclosure, for holding a test subject, defined by multiple boundary surfaces;
    a maze having at least two removable obstacles under control of a programmable system that configures the maze by inserting or removing at least one of the at least two obstacles through a boundary surface of the maze ; and
    a controller having a logic system configured to control design of the maze without manual input from a user.

28. A dynamic maze for studying a test subject, comprising:
    a programmable flooring having a plurality of floor plates such that each floor plate is capable of being a reward or punishment to the test subject traversing the maze.

29. The maze of claim 28 wherein the flooring is programmable manually by a user.

30. The maze according to claim 28 wherein the flooring is responsive to the behavior of the test subject traversing the maze.

31. A dynamic maze, comprising:
    an interior maze volume defined by multiple boundary surfaces;
    at least two removable obstacles under control of a programmable system that configures the maze by inserting or removing at least one of the at least two obstacles through a boundary surface of the maze; and
    a controller having a logic system configured to control design of the maze.

32. The maze according to claim 31 further comprising:
    at least one tube disposed thereon, the tube configured to entrap a test subject such that the test subject can only traverse through the tube in one direction.

33. The maze according to claim 32 wherein two or more tubes are interconnected.

34. The maze according to claim 32 wherein at least one tube is rotatable.

35. The maze according to claim 32, wherein the tube further comprises:
    at least one floor plate capable of being an obstacle.

36. The maze according to claim 31, further comprising:
    at least one incline means, the incline means configured to be an obstacle to a test subject in the maze such that the incline means is responsive to ability of the test subject to traverse through the maze.

37. The maze according to claim 36, wherein the incline means comprises:
   at least one floor plate.
38. The maze according to claim 31, further comprising:
   at least one flooring such that the flooring is movable for creating an obstacle for a test subject traversing through the maze.
39. The maze according to claim 31, wherein the flooring further comprises:
   at least one stilt that is rotatable about the flooring such that the stilt creates an obstacle for a test subject.
40. The maze according to claim 39, wherein the stilt is adjustable to various angles in relationship to the flooring.
41. The maze according to claim 31, further comprising:
   a collapsible flooring, the flooring being able to expose a wall that creates an obstacle for the test subject.
42. The maze according to claim 41, further comprising:
   a user interface for manual operation of the collapsible flooring.
43. The maze according to claim 41, wherein the controller controls the collapsible floor based on the behavior of the test subject traversing the maze.
44. The maze according to claim 31, further comprising:
   an integrated light source in at least one floor plate.
45. The maze according to claim 44 wherein intensity of said integrated light source is variable.
46. The maze according to claim 44 wherein intensity of said integrated light source is programmable by said controller.
47. The maze according to claim 31, further comprising:
   a shock providing mechanism.
48. The maze according to claim 47 wherein intensity of said shock providing mechanism is variable.
49. The maze according to claim 47 wherein intensity of said shock providing mechanism is programmable by said controller.
50. A method of re-configuring a maze, comprising:
   receiving data from a test subject in the maze; and
   re-configuring design of the maze by inserting or removing at least one obstacle from the maze through a boundary surface of the maze, based on the data without intervention from a user.
51. The method according to claim 50, wherein the data is transmitted from the maze.
52. A method of assessing the ability of a test subject to solve a maze, comprising:
   delivering at least one of rewarding or noxious stimulus to the test subject depending on path taken by the test subject in the maze; and
   re-configuring the maze without user intervention based on ability of the test subject to traverse through the maze.
53. The method of claim 52 further comprising the step of:
   delivering a secondary stimulus to the test subject to enforce or conflict effect of said rewarding or noxious stimulus.
54. A method to assess ability of an animal to solve mazes of differing complexities, comprising:
   recording ability of a test subject to traverse through a maze; and
   re-configuring the maze without user intervention to various levels of complexity based on the ability of the test subjects to traverse the maze.
55. The method of claim 54 further comprising the step of:
   delivering rewarding or noxious stimulus to the test subject depending on path taken by the test subject in the maze.
56. The method of claim 54 further comprising the step of:
   measuring time required by the animal to solve the maze.
57. A dynamic maze, comprising:
   an interior maze volume defined by multiple boundary surfaces; and
   at least two removable obstacles under control of a programmable system that configures the maze by inserting or removing at least one of the at least two obstacles through a boundary surface of the maze such that the maze rapidly re-configures for measurement of different behavioral responses of a test subject.
58. The dynamic maze according to claim 57, wherein the obstacle vibrates.
59. The dynamic maze according to claim 57, wherein the obstacle is a moving single floor.
60. The dynamic maze according to claim 59, wherein the flooring moves in a single direction.
61. The dynamic maze according to claim 59, wherein the flooring moves in multiple directions.
62. The dynamic maze according to claim 57, wherein the obstacle further comprises:
   a plurality of moving floor plates.
63. The dynamic maze according to claim 62, wherein the floor plates move in concert.
64. The dynamic maze according to claim 62, wherein the floor plates move individually such that at least one floor plate is still and at least another floor plate is moving.
65. The dynamic maze according to claim 62, wherein the floor plates move individually.
66. The dynamic maze according to claim 62, wherein the floor plates move in different directions.
67. The dynamic maze according to claim 57, further comprising:
   a integrated light source in at least one floor plate.
68. The dynamic maze according to claim 57, further comprising:
   a shock providing mechanism.
69. A dynamic maze, comprising:
   at least one removable obstacle wherein the obstacle is under control of a programmable system that configures the maze by inserting the obstacle into the maze or removing the obstacle from the maze and wherein the obstacle transmits a primary stimulus to a test subject in a rewarding or noxious manner, and
   a secondary stimulus that can reinforce or conflict with the primary stimulus.
70. A dynamic maze, comprising:
   at least one removable obstacle wherein the obstacle is under control of a programmable system that configures the maze by inserting the obstacle into the maze or removing the obstacle from the maze;
   a controller having a logic system configured to control design of the maze; and
   at least one tube disposed thereon, the tube configured to entrap a test subject such that the test subject can only traverse through the tube in one direction.
71. The maze according to 70, wherein the tube further comprises:
   at least one floor plate capable of being an obstacle.
72. The maze according to claim 70, further comprising:
   at least one incline means, the incline means configured to be an obstacle to a test subject in the maze such that the incline means is responsive to ability of the test subject to traverse through the maze.

73. The maze according to claim 72, wherein the incline means comprises:
   at least one floor plate.

74. The maze according to claim 70, further comprising:
   at least one flooring such that the flooring is movable for creating an obstacle for a test subject traversing through the maze.

75. The maze according to claim 70, wherein the flooring further comprises:
   at least one stilt that is rotatable about the flooring such that the stilt creates an obstacle for a test subject.

76. The maze according to claim 75, wherein the stilt is adjustable to various angles in relationship to the flooring.

77. The maze according to claim 70, further comprising:
   a collapsible flooring, the flooring being able to expose a wall that creates an obstacle for the test subject.

78. The maze according to claim 77, further comprising:
   a user interface for manual operation of the collapsible flooring.

79. The maze according to claim 77, wherein the controller controls the collapsible floor based on the behavior of the test subject traversing the maze.

* * * * *